United States Patent [19]

Roberts

[11] Patent Number: 5,435,177
[45] Date of Patent: Jul. 25, 1995

[54] APPARATUS AND METHOD FOR TESTING SPRING PACKS OF MOTOR OPERATED VALVES

[75] Inventor: Jeffrey J. Roberts, Mishicot, Wis.

[73] Assignee: Wisconsin Electric Power Company, Milwaukee, Wis.

[21] Appl. No.: 205,860

[22] Filed: Mar. 3, 1994

[51] Int. Cl.⁶ .................. G01L 1/04; G01D 7/10; G01N 3/08; G01N 3/26
[52] U.S. Cl. ........................ 73/161; 73/168; 73/790; 73/791
[58] Field of Search ............... 73/161, 168, 790, 791

[56] References Cited

U.S. PATENT DOCUMENTS

| | | | |
|---|---|---|---|
| 2,920,482 | 1/1960 | Droke | 73/161 |
| 3,285,065 | 11/1966 | Ragen et al. | 73/161 |
| 3,640,129 | 2/1972 | Bandimere | 73/161 |
| 3,834,228 | 9/1974 | Wachholz | 73/161 |
| 4,157,033 | 6/1979 | Shereda et al. | 73/161 |
| 4,660,416 | 4/1987 | Charbonneau et al. | 73/168 |
| 4,690,003 | 9/1987 | McNennamy et al. | 73/862.32 |
| 4,860,596 | 8/1989 | Charbonneau et al. | 73/862.32 |
| 5,167,151 | 12/1992 | Hinant et al. | 73/161 |
| 5,168,761 | 12/1992 | Hinant et al. | 73/791 |

*Primary Examiner*—Diego F. F. Gutierrez
*Attorney, Agent, or Firm*—Quarles & Brady

[57] ABSTRACT

An apparatus, for testing a spring pack of a valve operator, includes a hollow housing with a coupling for attaching to the valve operator. A slider is received within the housing and moves therein when driven by a bolt that extends through a threaded aperture in the housing. A load sensor is attached to the slider and extends through the coupling and engages a valve operator component that is connected to the spring pack. As a technician turns the bolt, the apparatus compresses the spring pack within the valve operator and the load sensor produces an electrical signal that indicates how much force is exerted by the spring pack. At the same time, a transducer produces another electrical signal indicating the displacement of the spring pack.

16 Claims, 2 Drawing Sheets

APPARATUS AND METHOD FOR TESTING SPRING PACKS OF MOTOR OPERATED VALVES

BACKGROUND OF THE INVENTION

The present invention relates to testing of motor operated valves, and more particularly to apparatus for testing the spring pack used in such valves to verify that the spring pack is functioning with acceptable specifications.

Many motor operated valves contain a spring pack which is biased whenever torque is applied to the valve stem by the motor. A torque switch is coupled to the spring pack so that when a certain level of torque is reached, as occurs in the fully opened or fully closed positions of the valve, the torque switch stops the motor and prevents the application of more torque. Should the spring pack not conform to specifications, the torque switch will be inappropriately triggered. If the switch is triggered too early, the valve may not be in its fully open or fully closed position, thereby affecting flow through the valve. If the switch is triggered too late, the motor will be allowed to apply additional torque to the valve components, possibly damaging those components. Thus, it is important for the spring packs to accurately operate within their specified range.

In the past, spring packs typically were removed from the valve operator and placed in a special test stand to evaluate their performance. The test stand compressed the spring pack while measurements of the force exerted and the spring pack movement were recorded. This allowed a graph to be created of the spring pack force versus displacement. An example of a spring pack testing apparatus of this type is shown in U.S. Pat. No. 5,167,151. Afterwards, the data was evaluated either by itself or by comparing it to previous tests conducted on the same spring pack to determine changes with time. Depending upon the results of the evaluation, the spring pack was either re-inserted into the motor operated valve or discarded.

Motor operated valves are often used in very critical systems, such as those which control the flow of coolant in nuclear reactors used in electric utility generating stations. Very stringent requirements are placed on motor operated valves in these critical applications. In such installations, when the spring pack was re-inserted into the valve after testing, the operating mechanism had to be recalibrated and thoroughly inspected to insure proper functioning of the valve. This not only was time consuming procedure, but also expensive.

U.S. Pat. No. 4,860,596 shows an alternative method for testing the motor operated valve in which a load sensor was attached to a shaft which operated the torque limit switch. Although this type of tester eliminated the need to disassemble the valve operator and remove the spring pack, it did not directly measure the force exerted on the spring pack and further required that the valve be cycled through open and closed states. It is desirable in many installations to be able to test the spring pack directly to obtain measurements of its actual performance and without operating the valve so that the state of the fluid flow is unaffected during testing.

SUMMARY OF THE INVENTION

A general object of the present invention is to provide an apparatus and method for testing the spring pack of a motor operated valve while the spring pack is inside the valve operator.

Another object is to perform such testing without having to operate the valve and thus without affecting the flow of fluid through the valve.

A further object of the present invention is to provide an apparatus that directly measures the force versus displacement of the spring pack.

These objects are satisfied by a device that comprises a housing having a coupling for attaching to the valve operator. A load sensor is movably coupled to said housing and is adapted to engage a valve operator component that is connected to the spring pack. For example, during the testing process, the load sensor engages a shaft on which the spring pack is mounted. The load sensor produces a first electrical signal that indicates the amount of force being applied by the spring pack to the load sensor. A mechanism is connected to the housing to move the load sensor with respect to the housing and compress the spring pack within the valve operator. A transducer produces a second electrical signal indicating displacement of the load sensor with respect to said housing.

In the preferred embodiment of the present invention, the first and second electrical signals are digitized by an interface circuit and the digitized signals are fed to a computer. The computer records the digitized signals and displays the force applied by the spring pack as a function of the displacement. The results of the testing of the spring pack also can be compared to results of previous testing of the same spring pack in order to detect deterioration over time.

DETAILED DESCRIPTION OF THE INVENTION

Figure 1:
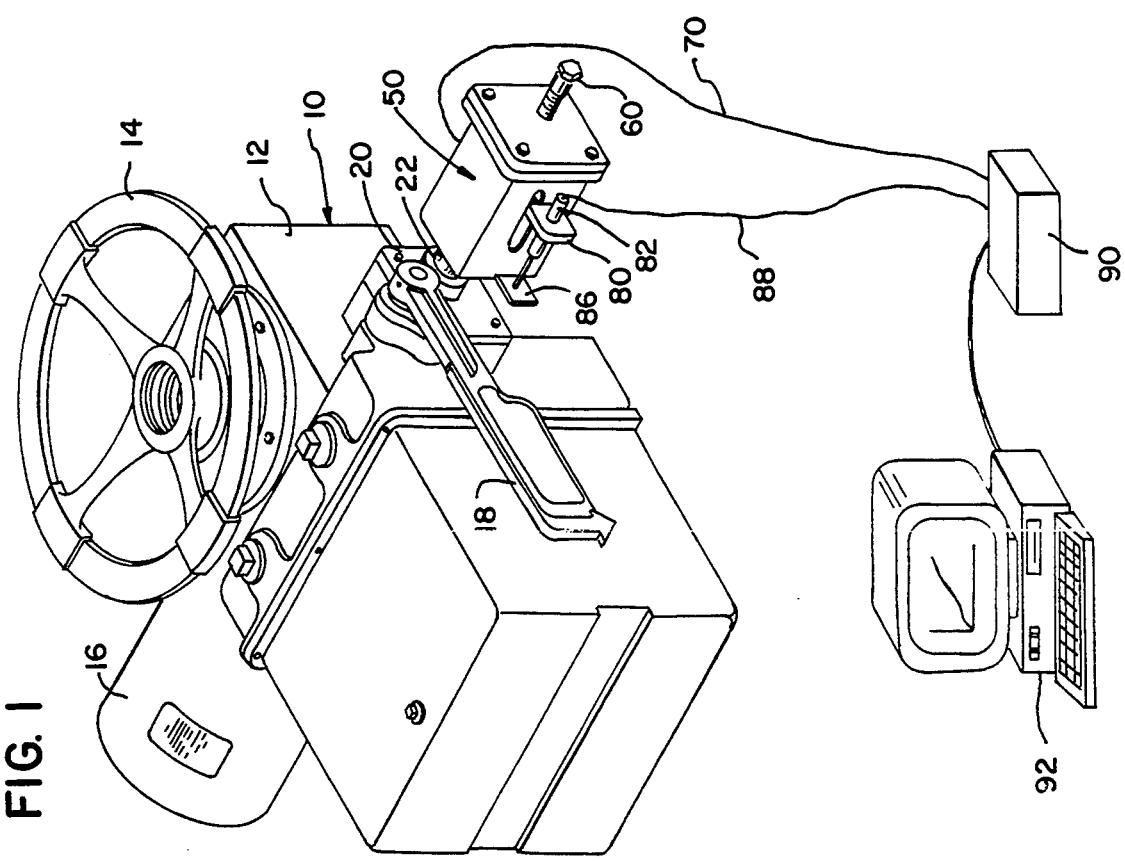
FIG. 1 illustrates a motor operated valve to which a testing according to the present invention is connected.

With initial reference to FIG. 1, a motor operated valve 10 has an operator 12 with a manual operating handle 14 and an electric motor 16. In a normal mode of operation, the electric motor 16 is connected by a clutch to the valve stem. When the motor is energized, the valve either opens or closes depending upon the direction of movement dictated by the energizing electricity. A technician is able to operate a clutch lever 18 to disengage the electric motor 16 from the valve stem and enable the handle 14 to manually open or close the valve.

The clutch lever 18 is attached to a shaft which passes through an external cover plate 20 over an opening in the enclosure of the valve operator 12. The cover plate 20 has been modified for use with the present testing device by providing a collar 22 with an aperture therethrough and through the cover plate. When the valve is not being tested, the collar has a plug inserted in its aperture. With the exception of the special cover plate 20, the motor operated valve 10 is of a conventional design.

Figure 2:
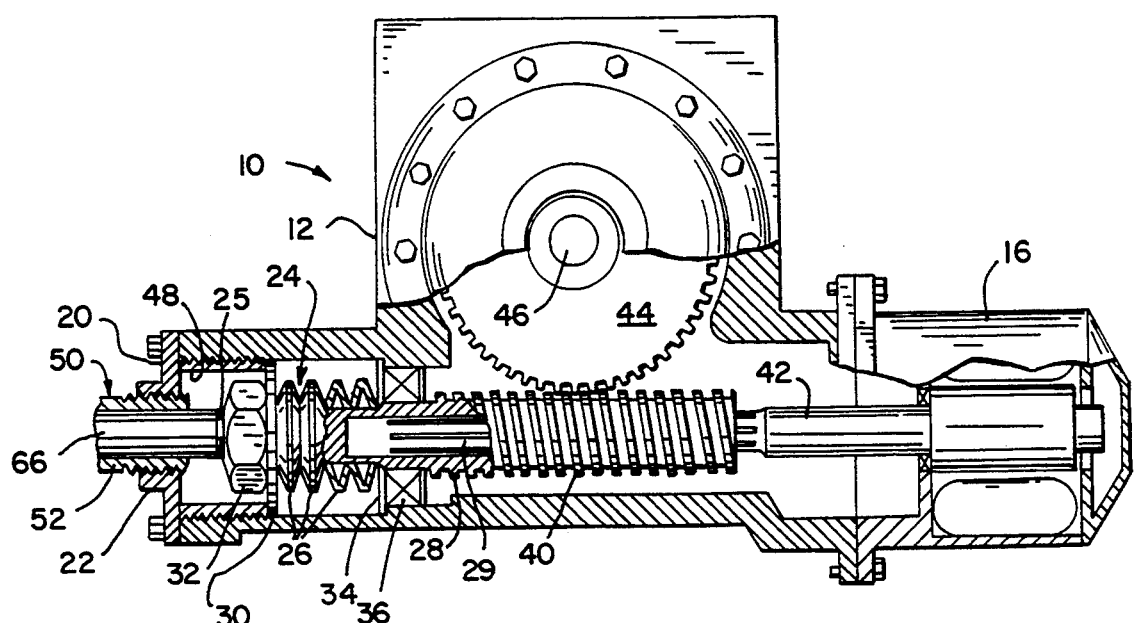
FIG. 2 is a cross-sectional view through part of the motor operated valve.

As shown in FIG. 2, the cover plate 20, which is held onto the valve operator 12 by several bolts, extends over an opening which allows access to the spring pack 24. The spring pack 24 consists of a number of Belleville springs 26 placed around the end of a worm shaft 28 and held in place by a first washer 30 and nut 32 on end 25 of the shaft. The spring pack also abuts a second washer 34 that is against a shoulder of the worm shaft 28 near bearing 36. A worm 40 is cut into the portion of the shaft 28 that is on the opposite side of the bearing 36 from spring pack 24. The worm 40 engages a worm gear 44 that is connected to the stem 46 of the valve by the clutch (not shown). The portion of the shaft 28 with worm 40 also has a longitudinal splined aperture 29. A shaft 42 of the motor 16 has external splines which fit into and engage the splined aperture of the shaft 28.

As the motor 16 turns in one direction, the worm 40 rotates the worm gear 44, thereby turning the valve stem 46. The force required to turn the worm gear 44 causes the worm shaft 28 to move longitudinally along with splines of the motor shaft 42 which in one direction of rotation draws the end 25 of the worm shaft 28 toward bearing 36 compressing the spring pack 24. In the other direction of motor rotation, the second washer 34 compresses the spring pack against the first washer 30 that is held in place by a tubular lock nut 48.

When the valve stem 46 reaches the fully closed or opened positions, the valve stem 46 will abruptly stop and even though the current from the motor 16 is interrupted, the rotational and kinetic energy of the operating mechanism causes the worm gear 44 to induce additional loads on the valve stem. The spring pack 24 is provided to absorb this energy and is compressed by the worm shaft 28 as the inertia of the operating mechanism attempts to move the valve stem 46.

With reference to FIGS. 1 and 2, in order to perform a test of the spring pack to insure that it is functioning properly, a test device 50 is threaded into the aperture in the collar 22 on cover plate 20. Conventional motor operated valves do not have a collar 22 on the cover plate 20. To configure the valve for testing, the conventional cover plate can be replaced with one having a collar 22. Alternatively, the conventional cover plate can be loosened and rotated around the shaft of the clutch during testing. Then a partial plate with a collar 22 is bolted over the exposed opening in the valve operator 12 in order to attach the testing device 50.

Figure 3:
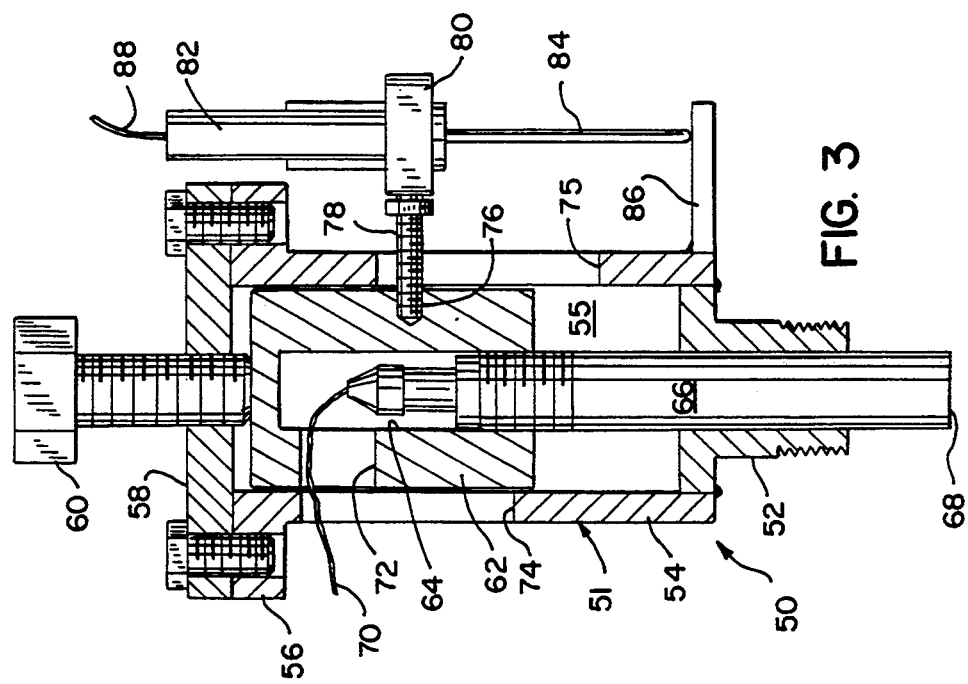
FIG. 3 is a cross section through part of the testing apparatus.

FIG. 3 illustrates the details of the test device 50 which includes a housing 51 formed by a mounting bushing 52, a body 54 and an end plate 58. The mounting bushing 52 has external threads which engage the threads of the aperture in the end plate collar 22 to fixedly connect the device 50 to the valve operator 12. The mounting bushing 52 is welded to one end of the hollow, tubular body 54 with another end 56 across which the end plate 58 is bolted. The end plate 58 has a central threaded aperture therethrough within which is located a drive bolt 60. A slider block 62 is within the housing 51 and has a cross section which conforms to, but is slightly smaller than the cross section of the internal chamber 55 of the housing. This enables the slider block 62 to move longitudinally within the housing 51.

The slider block 62 has an aperture 64 therein which is threaded at an open end to receive a conventional load sensing stud 66. The load sensing stud 66 extends from the slider block 62 through the central opening in the mounting bushing 52 and projects from the testing device 50. The load sensing stud, such as one produced by Strainsert Company includes internal strain gauges for sensing the compressive force applied longitudinally to the load sensing stud. A cable 70 that is connected to the strain gauges passes through apertures 72 and 74 in the slider block 62 and housing 51, respectively. When the testing device 50 is assembled onto the valve operator 12, the exposed end 68 of the load sensing stud passes through the collar 22 and lock nut 48 to abut the end of the worm shaft 28 as shown in FIG. 2.

One side of the slider block 62 shown in FIG. 3 has an aperture 76 which receives a bolt 78 that passes through a slot 75 in body 54 and attaches to an external mounting bracket 80. The mounting bracket 80 holds a slider type potentiometer 82 which acts as a transducer that senses displacement of the spring pack. The wiper of the potentiometer 82 is spring loaded and is attached to a sensing rod 84 that extends from the potentiometer. The sensing rod abuts a stop 86 which is attached to the end of the body 54 adjacent the mounting bushing 52. Thus, the wiper moves as the slider block moves within the housing and the resistance of the potentiometer varies with that movement.

With reference to FIG. 1, the cable 70 from the load sensing stud 68 and cable 88 from the potentiometer 82 are connected to a transducer interface 70 which in turn is connected to a personal computer 92. The transducer interface 90 consists of a power supply, signal conditioning modules, connectors and appropriate wiring and circuitry to provide precise excitation voltages to the load sensing stud 68 and the potentiometer 82. The transducer interface 90 and the software executed by the personal computer 92 are similar to previous systems which tested the spring pack upon removal from the motor operated valve, such as the system described in U.S. Pat. No. 5,167,151 which description is incorporated herein by reference. For convenience, the signals from the transducer interface 90 can be stored in a data recorder at the valve site and subsequently transferred to a computer in an office.

As noted previously, in order to test the spring pack 24, the test device 50 is attached to the motorized valve operator 12 by threading the mounting bushing 52 into the aperture of the collar 22 on the cover plate 20. The technician then places the valve clutch lever 18 into the position which disengages the worm gear 44 from the valve stem 46. This disengagement of the clutch allows the worm gear to turn freely as the spring pack 24 is compressed by the testing device 50 without affecting the state of the valve.

Then a technician applies a wrench to bolt 60 and begins turning the bolt into the end plate 58. The internal end of the bolt 60 pushes the slider block 62 toward the valve operator 12 so that the load sensing stud 66 abuts the end 25 of the worm shaft 28 as shown in FIG. 2. Further turning of the drive bolt 60 applies force to the worm shaft 28 and compresses the spring pack 24 between washers 30 and 34.

As the spring pack compresses, the transducer interface 90 receives the analog signal from the load sensing stud 66 which corresponds to the amount of force applied longitudinally to the load sensing stud by the spring pack 24. The transducer interface digitizes that analog signal to produce multiple bit digital numbers which are read periodically by computer 92 and stored in the computer's memory. The electrical signal produced by the potentiometer 82 also is converted into multiple bit digital numbers which also are periodically read and stored by computer 92. This action produces a series of paired data values that represent the spring pack force at different displacements as the bolt 60 is being turned.

The technician continues to turn the drive bolt 60 into the cover plate 58, applying greater force to compress the spring pack 24. As the spring pack is compressed, it exerts greater force on the load sensing stud 68 which is read by the computer 92 along with the displacement of the spring pack as indicated by the signal from potentiometer 82. In addition to receiving information from the load sensing stud and potentiometer, the computer 92 may also periodically sample the signal produced by the valve operator's torque switch, which samples also can be correlated to the force exerted by the spring pack and the displacement. All of the data collected by the computer 92 can be stored, analyzed, viewed graphically. The data may also be printed out both numerically or graphically from the computer 92. The data from the present test is compared by the computer with standards and results of previous tests on the same valve. Such comparison allows the spring pack deterioration over time to be ascertained and a determination made when to replace the spring pack as it approaches the end of its useful life.

Once the spring pack has been fully compressed, the technician backs the drive bolt 60 out of the cover plate 58, releasing compression on the spring pack 24. The testing device 50 then can be removed from the valve operator 12 and the plug re-inserted in the aperture of collar 22. The valve may have to be cycled following the testing procedure in order to properly reseat the spring pack 24 with respect to the position of the valve.

The present testing apparatus has several advantages over previous spring pack testing systems. The primary advantage is that the spring pack is tested within the motor operated valve 10, thereby eliminating the need to disassemble and reassemble the valve operator. This also eliminates the need to accurately position the spring pack lock nut 48 during reassembly and calibrate the valve operator as required by government regulations which apply to certain valve applications. In addition, the testing may occur without changing the flow state of the valve, and thus the valve can remain in service during the test procedure.

I claim:

1. A device for testing a spring pack mounted on a shaft of a valve operator, the device comprising:
   a housing with a coupling for attaching to the valve operator;
   a load sensor, movably coupled to said housing, for engaging one of the shaft and a valve operator component on the shaft to which the spring pack is mounted and producing a first electrical signal indicating an amount of force applied by the spring pack to said load sensor;
   a transducer which produces a second electrical signal indicating displacement of said load sensor with respect to said housing; and
   a mechanism for moving said load sensor with respect to said housing and compressing the spring pack within the valve operator.

2. The device as recited in claim 1 wherein said coupling comprises a mounting bushing with external threads that engage threads of an aperture in the valve operator.

3. The device as recited in claim 1 wherein said load sensor is movably coupled to said housing by a slider block slideably located within said housing, and said load sensor is attached to said slider block and projects through an aperture in said housing.

4. The device as recited in claim 3 wherein said transducer engages said slider block and said housing.

5. The device as recited in claim 3 wherein said mechanism comprises a bolt threaded through an aperture in said housing and applying force to said slider block.

6. The device as recited in claim 1 further comprising a plate which attaches to the valve operator and which engages the coupling of said housing.

7. The device as recited in claim 1 wherein said housing comprises a tubular body having an interior chamber; a threaded bushing attached to one side of said body to form said coupling; and an end plate attached to another side of said body.

8. The device as recited in claim 7 further comprising a slider block movably received within the interior chamber of said body, and said load sensor is attached to said slider block and projects through said bushing.

9. The device as recited in claim 8 wherein said end plate has a threaded aperture therethrough; and said mechanism comprises a bolt received in the threaded aperture and engaging said slider block.

10. The device as recited in claim 8 wherein said transducer engages said slider block and said housing to detect movement therebetween.

11. An apparatus for testing a spring pack of a valve operator, the apparatus comprising:
    a housing having a coupling for attaching to the valve operator;
    a load sensor, movably coupled to said housing, for engaging a valve operator component that is connected to the spring pack, said load sensor producing a first electrical signal indicating an amount of force applied by the spring pack to said load sensor;
    a transducer which produces a second electrical signal indicating displacement of said load sensor with respect to said housing;
    a mechanism for moving said load sensor with respect to said housing to compress the spring pack within the valve operator;
    an interface circuit connected to receive the first electrical signal from said load sensor and the second electrical signal from said transducer, and convert the first and second electrical signals into digital signals; and
    an display device connected to said interface circuit to receive the digital signals and display the force applied by the spring pack and the displacement of the spring pack.

12. The device as recited in claim 11 wherein said load sensor comprises a slider block movably located within said housing; and a load sensing stud attached to said slider block and projecting through an aperture in said housing.

13. The device as recited in claim 12 wherein said transducer engages said slider block and said housing.

14. A method for testing a spring pack mounted on a shaft of a valve operator, the method comprising:
    attaching a housing of a testing device via a coupling to the valve operator;
    engaging a load sensor, which is movably coupled to said housing, with one of the shaft and a valve operator component on the shaft to which the spring pack is mounted;
    producing, from said load sensor, a first electrical signal which indicates an amount of force applied by the spring pack to said load sensor;

producing, from a transducer of the testing device, a second electrical signal indicating displacement of said load sensor with respect to said housing; and employing a mechanism of the testing device to move said load sensor with respect to said housing and thereby compress the spring pack within the valve operator.

15. The method as recited in claim 14 further comprising periodically storing values representing the amount of force applied by the spring pack to said load sensor, and periodically storing values representing displacement of said load sensor with respect to said housing.

16. The method as recited in claim 15 further comprising comparing the stored values representing the amount of force and the displacement to other values representing the amount of force and the displacement during a previous testing of the spring pack.

* * * * *